United States Patent [19]

Sommer et al.

[11] 4,329,257

[45] May 11, 1982

[54] METHOD OF PRODUCING A CATALYST FROM CLAY MINERALS FOR THE HYDRATION OF OLEFINS

[75] Inventors: August Sommer; Wilhelm Heitmann, both of Herne; Rainer Brücker, Castrop-Rauxel, all of Fed. Rep. of Germany

[73] Assignee: Chemische Werke Huls Aktiengesellschaft, Kreis Recklinghausen, Fed. Rep. of Germany

[21] Appl. No.: 171,287

[22] Filed: Jul. 23, 1980

[30] Foreign Application Priority Data

Jul. 24, 1979 [DE] Fed. Rep. of Germany ....... 2929919

[51] Int. Cl.$^3$ .......................... B01J 27/14; B01J 29/00
[52] U.S. Cl. .................................................... 252/435
[58] Field of Search ................................ 252/435, 450

[56] References Cited

U.S. PATENT DOCUMENTS

| | | | |
|---|---|---|---|
| 2,147,783 | 2/1939 | Combron et al. | 252/450 |
| 2,377,092 | 5/1945 | McGraw | 252/435 X |
| 2,397,505 | 4/1946 | Richardson | 252/450 X |
| 2,466,047 | 4/1949 | Schobaker et al. | 252/450 |
| 2,748,090 | 5/1956 | Watkins | 252/435 X |
| 2,967,156 | 1/1961 | Talvendeimo et al. | 252/450 X |
| 3,560,586 | 2/1971 | Kronig et al. | 252/435 X |
| 3,704,329 | 11/1972 | Rindtorff | 252/435 X |
| 4,142,994 | 3/1979 | Alafandi | 252/450 |
| 4,235,751 | 11/1980 | Del Pesco | 252/450 |

FOREIGN PATENT DOCUMENTS

| | | |
|---|---|---|
| 2625705 | 12/1976 | Fed. Rep. of Germany . |
| 2719055 | 10/1977 | Fed. Rep. of Germany . |
| 2658946 | 6/1978 | Fed. Rep. of Germany . |
| 463272 | 3/1937 | United Kingdom ................ 252/435 |

Primary Examiner—Delbert E. Gantz
Assistant Examiner—William G. Wright
Attorney, Agent, or Firm—Oblon, Fisher, Spivak, McClelland & Maier

[57] ABSTRACT

A method for producing a catalyst comprising phosphoric acid and a carrier, for the hydration of olefins with 2-3 carbon atoms to the corresponding alcohols, the method comprising:

contacting a clay, containing essentially montmorillonite, contaminated by no more than 3% accompanying minerals and containing up to 0.5% by weight $K_2O$, or a mineral of the montmorillonite group, containing no potassium, but having the montmorillonite crystalline lattice, with an acid until it has an $Al_2O_3$ content of 13-18% by weight and a surface area of 200-400 m$^2$/g;

admixing the so-treated clay with 5-15% by weight, based on the total dry admixture, of one or more oxides of metals of Group VI of the Periodic System;

adjusting the water content of the admixture to 20-35% by weight;

pressing the admixture into a desired shape and calcining at 500°-800° C.;

treating the so-formed carrier material with an acid until it has an $Al_2O_3$ content of 1-5% by weight and a specific surface area of 150-250 m$^2$/g; and then impregnating the resulting carrier with phosphoric acid; and the catalysts so-produced are disclosed.

12 Claims, No Drawings

METHOD OF PRODUCING A CATALYST FROM CLAY MINERALS FOR THE HYDRATION OF OLEFINS

BACKGROUND OF THE INVENTION

1. Field of the Invention

This invention relates to a method for producing a catalyst for the hydration of olefins from clay minerals.

2. Description of the Prior Art

It is known that olefins in the gaseous phase can be converted under high pressures with steam into alcohols. Such methods have special technical significance in the production of ethyl alcohol from ethylene and isopropyl alcohol obtained from propylene. These alcohols are synthesized in the presence of catalysts, usually phosphoric acid provided on carriers.

Suitable carrier materials are based on pure silicic acid (e.g. diatomaceous earth or silica gel) or on silicic acid with greater or lesser clay content, such as calcined diatomaceous earth, whose structure is held together by clay or clay-like materials.

Long-term solidity is a problem with carrier materials based on pure silicic acid. The clay-containing materials have better mechanical solidity, however, they have the disadvantage that when their clay-content is too high aluminum oxide is dissolved away during the reaction due to the action of the phosphoric acid.

German Pat. No. 1 156 772 describes a method for producing a clay-containing carrier for phoshoric acid used as a catalyst in olefin hydration, in which molded contact bodies made of mineral clay silicates are treated with mineral acid so that the aluminum oxide content falls preferably to between 1 and 5% by weight (b.w.). This material generally has the necessary mechanical solidity and a sufficiently low residual aluminum oxide content to avoid dissolving away. In contrast it has been observed with the use of customary contact bodies in the production of catalyst carriers for olefin hydration, that without preselecting the raw material, strongly differing catalyst activities are produced.

Success was finally found in developing carriers for phosphoric acid on the basis of large pore silica gels with high hydration activity and adequate mechanical solidity, e.g. DE-OS No. 26 25 705 and DE-OS No. 27 19 055. Nonetheless, one disadvantage remained with these carriers based on amorphous silicic acid: upon extended exposure to the rigors of the hydration reaction, the amorphous silicic acid crystallised into cristobalite and quartz. This brought with it an irreversible, stark reduction of specific surface area and thus, catalytic activity, along with a decrease in mechanical solidity. Another disadvantage of all previously used hydration catalysts based on phosphoric acid on silicate carriers is the slow reduction of activity owing to dissipated phosphoric acid. Phosphoric acid must be continuously neutralized by alkali treatment in continuous operation in order to avoid the corrosive actions of acid and raw alcohol on the down stream distillation apparatus.

The more recent development of continuous spraying of washed-away phosphoric acid according to DE-OS No. 26 58 946 made it possible to avoid, to a large extent, the continuous loss of activity and, thus, to considerably extend the life span of the catalyst. This, however, places corresponding demands on the life span of the carrier, thus eliminating the use of such carriers as those with which crystallization occurs under reaction conditions, thereby irreversibly lessening the catalytic activity and the mechanical solidity in the course of time.

German patent application No. P 29 08 491.1 shows that a carrier for a hydration catalyst with continuing high catalytic activity can be produced from clay material when care is taken in the selection of the raw material to assure that the material consists largely of montmorillonite, which means that after being formed, macerated (leached) and impregnated, the active surface area on which the hydration of the olefins can take place is large.

German patent application No. P 29 08 491.1 relates to a method for producing a catalyst from clay minerals for the hydration of olefins with 2-3 C-atoms to the corresponding alcohols of phosphoric acid and carrier material—including the correspondingly produced catalyst—in which a clay containing essentially montmorillonite, contaminated by no more than 3% accompanying minerals such as quartz, feldspar and mica, and containing up to 0.5% of $K_2O$, is processed in a first step with acid until it has an $Al_2O_3$-content of 13–18% b.w. and, if necessary, the $Al_2O_3$—content is adjusted to 16–18% b.w. through the addition of precipitated clay. The result is a surface area of 200–400 $m^2/g$, preferrably 240–300 $m^2/g$. When the total water content is 20–35% it is pressed into a form, calcined at 500°–800° C., and the formed carrier material is then treated with acid in a second step until the $Al_2O_3$-content reaches 1–5% b.w., preferrably 1–3% b.w. The result is a surface area of 150–250 $m^2/g$, preferrably 180–220 $m^2/g$. Finally, the resulting carrier is impregnated in a known manner with phosphoric acid.

A different mineral in the montmorillonite group, which nonetheless, contains the montmorillonite crystalline lattice, can be used instead of montmorillonite.

It is also possible to use a fuller's earth or clay that has already been treated once with acid in place of a clay containing montmorillonite that has not yet been treated with acid. This makes the first acid treatment superfluous. This fuller's earth or clay should contain less than 0.1% $K_2O$; the weight ratio should be ($Al_2O_3+Fe_2O_3$): $SiO_2=1:3.5-1:4.5$. If needed, the $Al_2O_3$—content in the fuller's earth or clay can be brought to the necessary 16–18% b.w. by adding precipitated clay.

Catalyst or catalyst carriers produced in this way from clay containing montmorillonite have a different origin than those formed contact bodies based on mineral clay silicates, increased activity, i.e. per hour and 1 catalyst charging approximately 105–110 g of ethanol or ca. 300 g of isopropyl alcohol were produced. This increased activity, however, can only be sustained over an extended period if the phosphoric acid that is carried away—amounting to ca. 0.07 g per hr and 1 catalyst charging with ethanol—is constantly balanced by continuous replacement of an equal amount of acid. In addition, this dissipated acid must still be neutralized with an alkali treatment.

The mechanical solidity of the catalysts lies in the range of 7-9 kg/ball, which is sufficient to charge a customary reactor.

DETAILED DESCRIPTION OF THE PREFERRED EMBODIMENT

Surprisingly it has now been found that additional characteristics of the finished catalyst can be improved by adding 5–15% b.w. of the total dry substance of an oxide or a mixture of several oxides of elements in group VI of the periodic system. Therefore, it is the object of the invention to provide a method for producing a catalyst from clay materials for the hydration of olefins with 2-3 C-atoms to the corresponding alcohols from phosphoric acid and carrier material, wherein clay, containing essentially montmorillonite and contaminated by no more than 3% accompanying minerals such as quartz, feldspar and mica and up to 0.5% $K_2O$, is treated in a first step with acid, and, if necesary, by adding precipitated clay, until it has an $Al_2O_3$—content of 13–18% b.w. and a surface area of 200–400 $m^2/g$, preferably 240–300 $m^2/g$. Then, 5–15% b.w., based on the total dry substance, of one or several oxides of metal in group VI of the periodic system are added. Then, with a total water content of 20–35%, it is pressure formed, calcined at 500°–800° C., and the formed carrier material is then treated in a second step with acid until it has an $Al_2O_3$-content of 1–5% b.w., preferrably 1–3% b.w., and a surface area of 150–250 $m^2/g$, preferrably 80–220 $m^2/g$. The carrier thus formed is impregnated in known manner with phosphoric acid.

Other minerals of the montmorillonite group, containing no postassium, but having the montmorillonite crystalline lattice, can also be used.

A type of fuller's earth or clay, produced from a clay with large amounts of montmorillonite, that has already been treated once with acid, can also be used in the place of a clay containing montmorillonite that has not yet been acid treated. This makes the first acid treatment superfluous. The fuller's earth or clay should contain less than 0.1% $K_2O$; the weight ratios should be $(Al_2O_3+Fe_2O_3): SiO_2=1:3.5-1:4.5$. If necessary, the $Al_2O_3$—content of the fuller's earth or clay can be brought to the necessary 16–18% b.w. by adding precipitated clay.

The invention provides the following advantages:

1. The mechanical solidity of the catalyst increases to about 11–13 kg/ball. This is significant in the use of higher catalyst charges.
2. The catalyst activity increases to ca. 130 g ethanol and ca. 350 g isopropyl alcohol per hr and 1 catalyst charging.
3. The depletion of phorphoric acid is reduced to about one half, i.e. with ethanol to about 0.035 g per hr and 1 catalyst charging, with isopropyl alcohol to about 0.005 g per hr and 1 catalyst charging.

In addition to binding the phosphoric acid more firmly to the carrier by way of the heteropoly acid of metal in periodic group VI, it is also surprising that the oxides of the metals in periodic group VI can be incorporated into the silicate lattice in such a manner that they are not dissolved away at all by the subsequent acid treatment. It is evident that a build up of heteropoly acid has commenced between the silicon and the oxides of elements in periodic group VI when calcined under the conditions set out above.

EXAMPLE I

A ground, natural, raw clay, which was chosen on the basis of laboratory experiments in which no more than 5 g of $K_2O$ per kg of original dry substance was extracted in an hour-long treatment with 20% hydrochloric acid at 82° C., was heated at 82° C. or an hour with a 20% hydrochloric acid solution, washed free of acid and dried. The amount of acid was calculated so that 8.4 moles of HCl were used for 1 kg of clay. The result was a material with a residual aluminum oxide (moiety) content of 16% b.w. and a specific surface area of 300 $m^2/g$:

15 parts of tungsten oxide ($WO_2$) were added to 100 parts of this dry material so that the mixture contained 13% b.w. of tungsten oxide. After moistening with 25% water, based on the total amount (i.e. addition of 33% of the dry substance as water), the material was pressed into cylindrical forms with a 4 mm diameter and 4 mm height and solidified by three hours of 600° C. heat treatment.

The contact bodies formed in this manner were treated twice with 20% hydrochloric acid for a total of one hour at 100°–110° C. and then rinsed acid free with water. After drying at ca. 110°–120° C. the cylinders had an aluminum oxide content of 2.7% b.w., the specific surface area was 215 $m^2/g$. The tungsten oxide content had increased to 15% b.w.

These formed bodies were then bathed and allowed to react in 60% b.w. phosphoric acid for two hours and then redried at ca. 110°–120° C. The $H_3PO_4$—content of the cylinders processed in this manner was 35% b.w. The intermediate compression resistance was 11 kg/cylinder.

When this hydration catalyst was applied in the synthesis of ethanol from ethylene and water in the gaseous phase, the catalyst yield was 130 g of ethanol per hr and 1 catalyst charging. Phosphoric acid dissipation under reaction conditions was 0.035 g per hr and 1 catalyst charging.

EXAMPLE 2

100 parts of a highly active fuller's earth or clay with a specific surface area of 350 $m^2/g$ and the following chemical analysis—72.5% $SiO_2$, 14.0% $Al_2O_3$, 4.0% $Fe_2O_3$, 1.5% MgO, 0.8% CaO, 7.2 loss on ignition, $K_2O$ 0.1%—were mixed with 8 parts of chromium oxide ($CrO_3$) so that the mixture contained 7.4% chromium oxide. After moistening with 30% water, based on the total amount (i.e. addition of 43% of the dry substance as water), the material was pressed into balls with a 4 mm diameter and solidified in 600° C. for 3 hours.

The contact bodies formed in this manner were treated twice with 20% hydrochloric acid for a total of one hour at 100°–110° C. and then rinsed acid free with water. After drying at ca. 110°–120° C. the balls had an aluminum oxide content of 1.4% b.w., the specific surface area was 230 $m^2/g$. The chromium oxide content had increased to 9% b.w.

These formed bodies were then bathed and allowed to react in 60% b.w. phosphoric acid for two hours and then redried at ca. 110°–120° C. The $H_3PO_4$—content of the balls processed in this manner was 36% b.w. The intermediate compression resistance was 13 kg/ball.

When this hydration catalyst was applied in the synthesis of ethanol from ethylene and water in the gaseous phase, the catalyst yield was 130 g of ethanol per hr and 1 catalyst charging. Phosphoric acid dissipation under reaction conditions was 0.035 g per hr and 1 catalyst charging.

EXAMPLE 3

100 parts of a highly active fuller's earth or clay with a specific surface area of 350 $m^2/g$ and the following chemical analysis—72.5% $SiO_2$, 14.0% $Al_2O_3$, 4.0% $Fe_2O_3$, 1.5% MgO, 0.8% CaO, 7.2% loss on ignition, $K_2O$ 0.1%—were mixed with 10 parts of molybdenum oxide ($MoO_3$) so that the mixture contained 7.4% of molybdenum oxide. After moistening with 30% water, based on the total amount (i.e., addition of 43% of the dry substance as water), the material was pressed into balls with a 4 mm diameter and solidified by 600° C. heat for 3 hours.

The contact bodies formed in this manner were treated twice with 20% hydrochloric acid for a total of one hour at 100°–110° C. and then rinsed acid free with water. After drying at ca. 110°–120° C. the balls had an aluminum oxide content of 1.4% b.w., the specific surface area was 230 m$^2$/g. The molybdnm oxide content had increased to 11% b.w.

These formed bodies were then bathed and allowed to react in 40% b.w. phosphoric acid for two hours and then redried at ca. 110°–120° C. The H$_3$PO$_4$—content of the balls processed in this manner was 27% b.w. The intermediate compression resistance was 12 kg/ball.

When this hydration catalyst was applied in the synthesis of isopropyl alcohol from propylene and water in the gaseous phase, the catalyst yield was 350 g of isopropyl alcohol per hr and 1 catalyst charging. Phosphoric acid dissipation under reaction conditions was 0.005 g per hr and 1 catalyst charging.

EXAMPLE 4

100 parts of a highly active fuller's earth or clay with a specific surface area of 350 m$^2$/g and the following chemical analysis—72.5% SiO$_2$, 14.0% Al$_2$O$_3$, 4.0% Fe$_2$O$_3$, 1.5% MgO, 0.8% CaO, 7.2% loss on ignition, K$_2$O 0.1%—were mixed with 3 parts chromium oxide (CrO$_3$), 3 parts molybdenum oxide (MoO$_3$), 5 parts tungsten oxide (WO$_3$), so that the mixture contained a total of 10% oxide of elements of periodic group VI.

After moistening with 30% water, based on the total amount (i.e. addition of 43% of the dry substance as water), the material was pressed into balls with a 4 mm diameter and solidified in 600° C. heat for 3 hours.

The contact bodies formed in this manner were treated twice with 20% hydrochloric acid for a total of one hour at 100°–110° C. and then rinsed acid free with water. After drying at ca. 110°–120° C. the content of oxides of elements of the VI periodic group had increased to 12% b.w.

These contact bodies were then bathed and allowed to react in 60% b.w. phosphoric acid for two hours and then redried at ca. 110°–120° C. The H$_3$PO$_4$—content of the balls processed in this manner was 35% b.w. The intermediate compression resistance was 13 kg/ball.

When this hydration catalyst was applied in the synthesis of ethanol from ethylene and water in the gaseous phase, the catalyst yield was 130 g of ethanol per hr and 1 catalyst charging. Phosphoric acid dissipation under reaction conditions was 0.035 g per hr and 1 catalyst charging.

What is claimed as new and intended to be covered by Letters Patent is:

1. A method for producing a catalyst comprising phosphoric acid and a carrier, for the hydration of olefins with 2–3 carbon atoms to the corresponding alcohols, the method comprising:
    contacting a clay, containing essentially montmorillonite, contaminated by no more than 3% accompanying minerals and containing up to 0.5% by weight K$_2$O, or a mineral of the montmorillonite group, containing no potassium, but having the montmorillonite crystalline lattice, with an acid until it has an Al$_2$O$_3$ content of 13–18% by weight and a surface area of 200–400 m$^2$/g;
    admixing the so-treated clay with 5–15% by weight, based on the total dry admixture, of one or more oxides of metals of Group VI of the Periodic System;
    adjusting the water content of the admixture to 20–35% by weight;
    pressing the admixture into a desired shape and calcining at 500°–800° C.;
    treating the so-formed carrier material with an acid until it has an Al$_2$O$_3$ content of 1–5% by weight and a specific surface area of 150–250 m$^2$/g; and
    then impregnating the resulting carrier with phosphoric acid.

2. The method according to claim 1, wherein after the first acid treatment, the clay has a surface area of 240–300 m$^2$/g.

3. The method according to claim 1, wherein after the second acid treatment, the carrier has a surface area of 180–220 m$^2$/g.

4. The method according to claim 1, wherein a clay, containing essentially montmorillonite, contaminated by no more than 3% accompanying minerals and containing up to 0.5% by weight K$_2$O, is contacted with an acid.

5. The method according to claim 1, wherein a mineral of the montmorillonite group, containing no potassium, but having the montmorillonite crystalline lattice, is contacted with an acid.

6. The method according to claim 1, wherein prior to admixture with one or more oxides of metals of Group VI, the Al$_2$O$_3$ content is adjusted to within the range of 13–18% by weight by the addition of precipitated clay.

7. A method for producing a catalyst comprising phosphoric acid and a carrier, for the hydration of olefins with 2–3 carbon atoms to the corresponding alcohols, the method comprising:
    adjusting the Al$_2$O$_3$ content of a highly active fuller's earth or clay, that has been acid treated, and is made from a clay with a high montmorillonite content, having less than 0.1% K$_2$O, whose weight ratio (Al$_2$O$_3$+Fe$_2$O$_3$):SiO$_2$ is in the range 1:3.5 to 1:4.5, and whose specific surface area is 200–400 m$^2$/g, to 16–18% by weight, by the addition of precipitated clay;
    admixing the fuller's earth or clay with 5–15% by weight, based on the total dry admixture, of one or more oxides of metals of Group VI of the Periodic System;
    adjusting the water content of the admixture to 20–35% by weight;
    pressing the admixture into a desired shape and calcining at 500°–800° C.;
    treating the so-formed carrier material with an acid until it has an Al$_2$O$_3$ content of 1–5% by weight and a specific surface area of 150–250 m$^2$/g; and
    then impregnating the resulting carrier with phosphoric acid.

8. The method according to claim 7, wherein the fuller's earth or clay has a specific surface area of 240–300 m$^2$/g.

9. The method according to claim 7, wherein the so-formed carrier material has an Al$_2$O$_3$ content of 1–3% by weight after acid treatment.

10. The method according to claim 7, wherein the so-formed carrier material has a specific surface area of 180–220 m$^2$/g after acid treatment.

11. The method according to claim 7, wherein prior to admixture with one or more oxides of metals of Group VI, the Al$_2$O$_3$ content is adjusted to within the range of 16–18% by weight by the addition of precipitated clay.

12. The catalyst for the hydration of olefins produced by the process of claims 1, 2, 3, 4, 5, 7, 8, 9, 10, 6 or 11.

* * * * *